United States Patent [19]
Cooper

[11] Patent Number: 5,702,249
[45] Date of Patent: Dec. 30, 1997

[54] MODULAR INTRA-ORAL IMAGING SYSTEM VIDEO CAMERA

[76] Inventor: David H. Cooper, 13668 Ronnie Way, Saratoga, Calif. 95070

[21] Appl. No.: 445,011

[22] Filed: May 19, 1995

[51] Int. Cl.$^6$ .................................................. A61C 3/00
[52] U.S. Cl. .............................. 433/29; 600/101; 600/172
[58] Field of Search ........................... 433/29; 600/109, 600/160, 167, 168, 170, 171, 172, 173, 175, 176, 101; 358/98

[56] References Cited

U.S. PATENT DOCUMENTS

| | | | |
|---|---|---|---|
| 3,804,081 | 4/1974 | Kinoshita et al. | 600/170 |
| 4,184,175 | 1/1980 | Mullane, Jr. | 433/29 |
| 4,398,811 | 8/1983 | Nishioka et al. | 600/170 X |
| 4,777,524 | 10/1988 | Nakajima et al. | 600/167 X |
| 4,838,247 | 6/1989 | Forkner | 600/171 |
| 5,049,070 | 9/1991 | Ademovic | 433/29 |
| 5,051,824 | 9/1991 | Nishigaki | 600/172 |

*Primary Examiner*—Nicholas D. Lucchesi
*Attorney, Agent, or Firm*—Raymond E. Roberts; Michael J. Hughes

[57] ABSTRACT

A hand held intra-oral video camera (10) is provided for capturing images from inside a dental patient's mouth which has a housing (24) having a distal end (26) and a handle portion (30). Within the distal end (26) a view port (32) is located and a sensor assembly (18) is mounted. The camera (10) may include a full featured objective assembly (14) and a main lens assembly (17), for suitably manipulating image content; a reflector (16) for capturing images from an angle substantially away from a longitudinal axis (12) of the housing (24); and, an illumination assembly (20) to illuminate the surface from which images are captured. The reflector (16) may provide mirrored or conventional image orientation. Wide angles of view, high resolution, and great depth of focus are provided by the camera (10) due to the absence within it of any purely image relaying optical elements. The camera (10) may integrate with other dental tools, either in permanent or temporary modular manner. The camera (10) may also be itself modularly constructed for ease in reconfiguring, or for ease of disposal, cleaning or sterilization of patient and operator contacting portions.

31 Claims, 12 Drawing Sheets

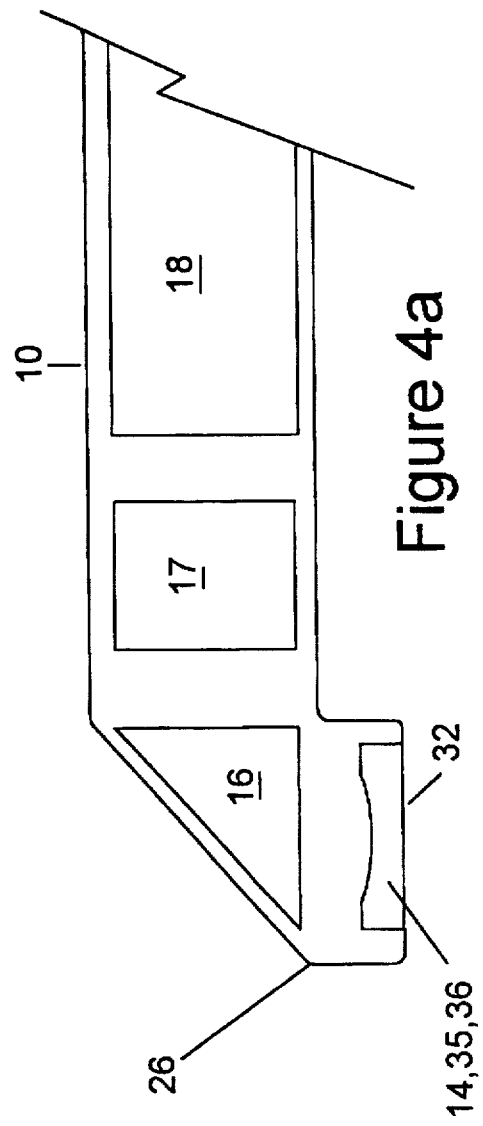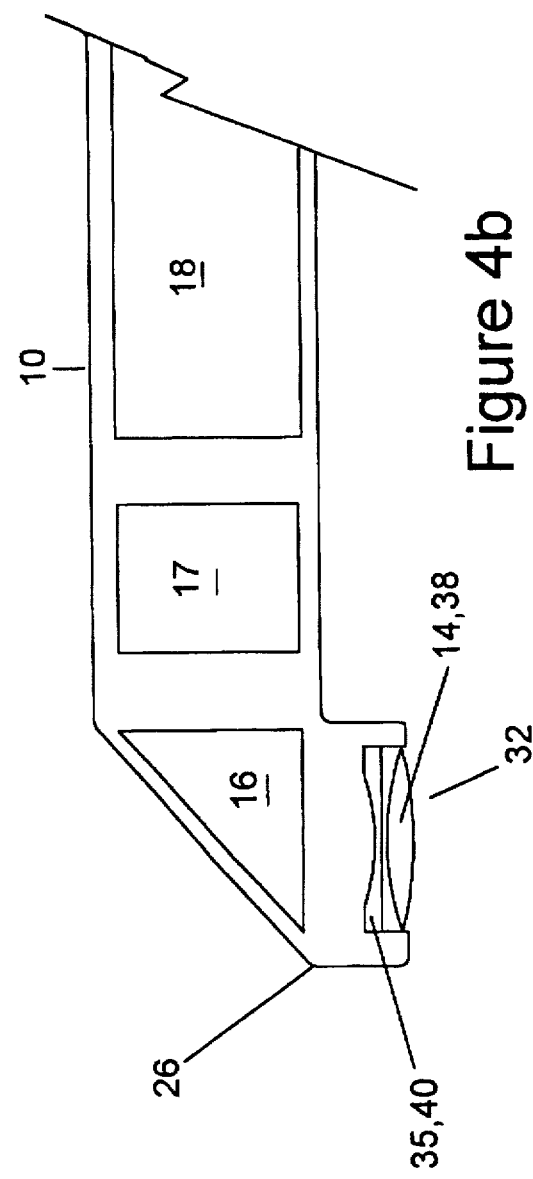

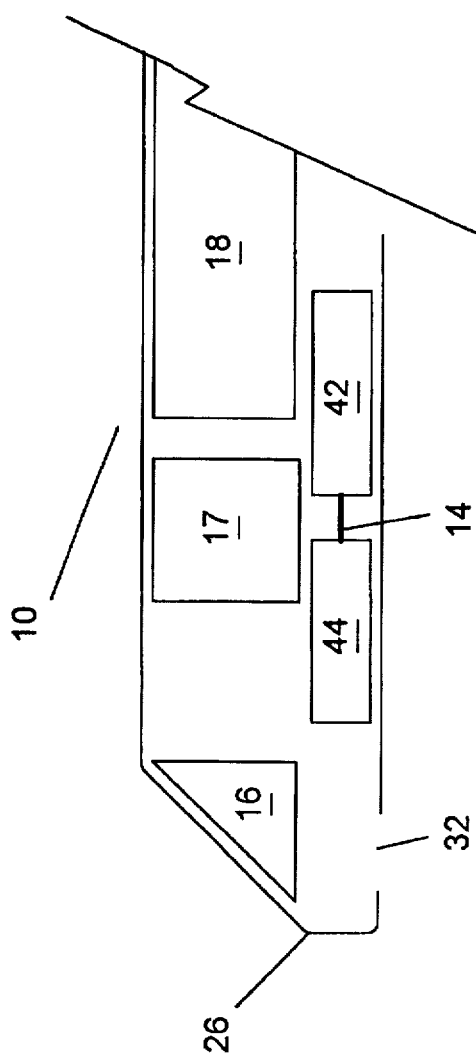
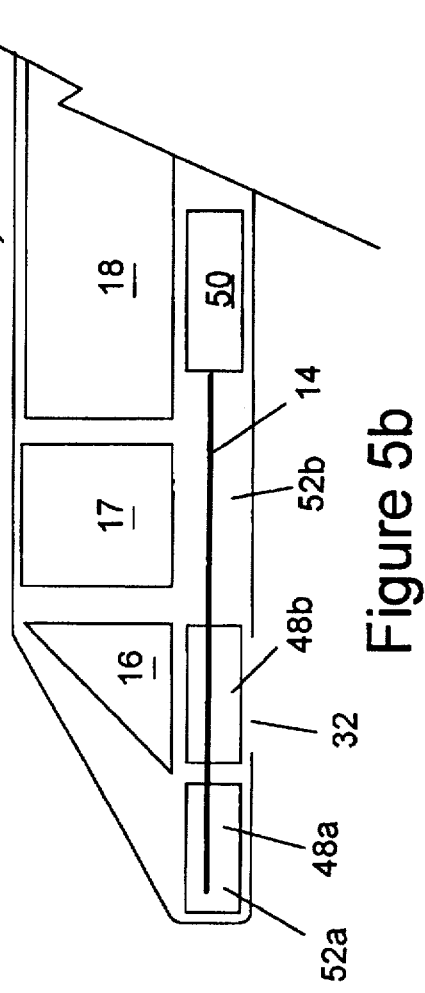

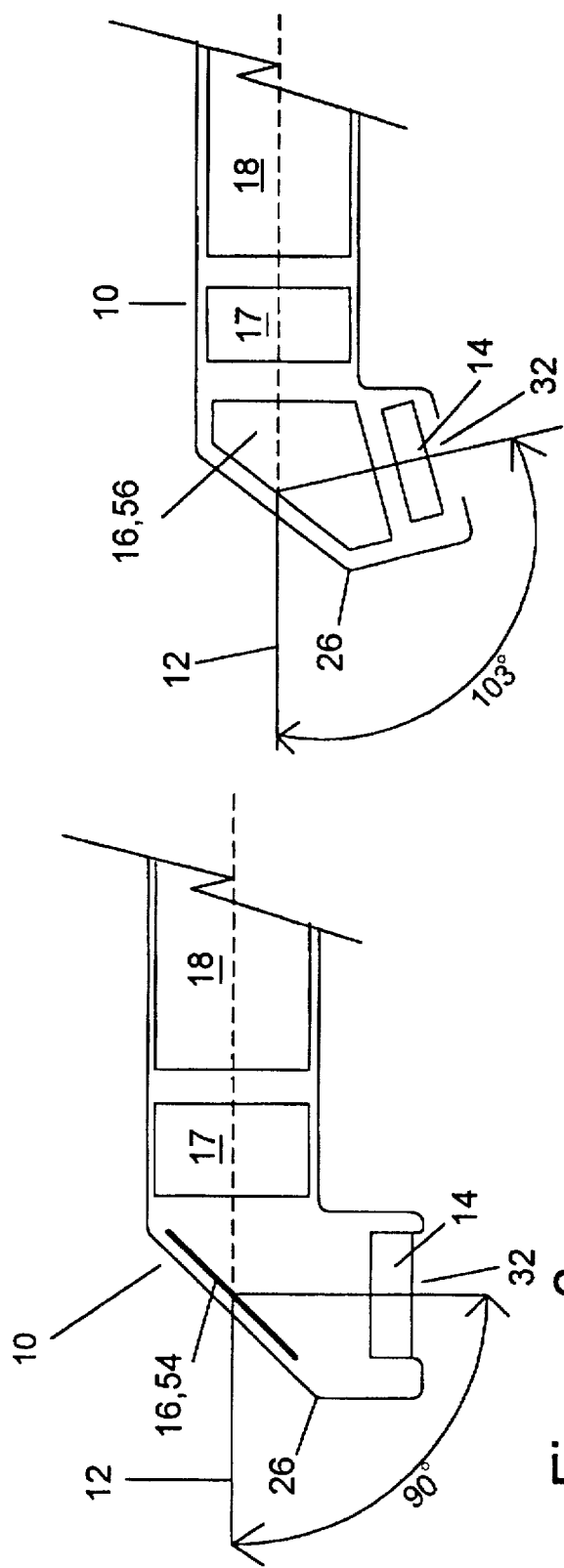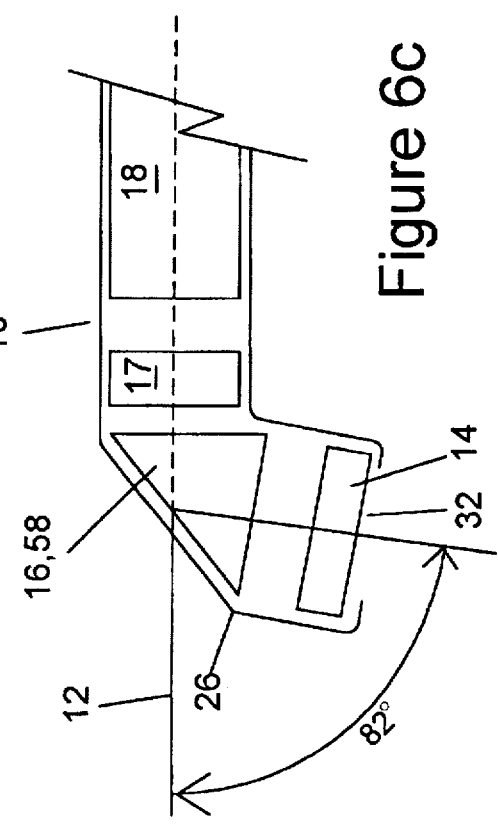

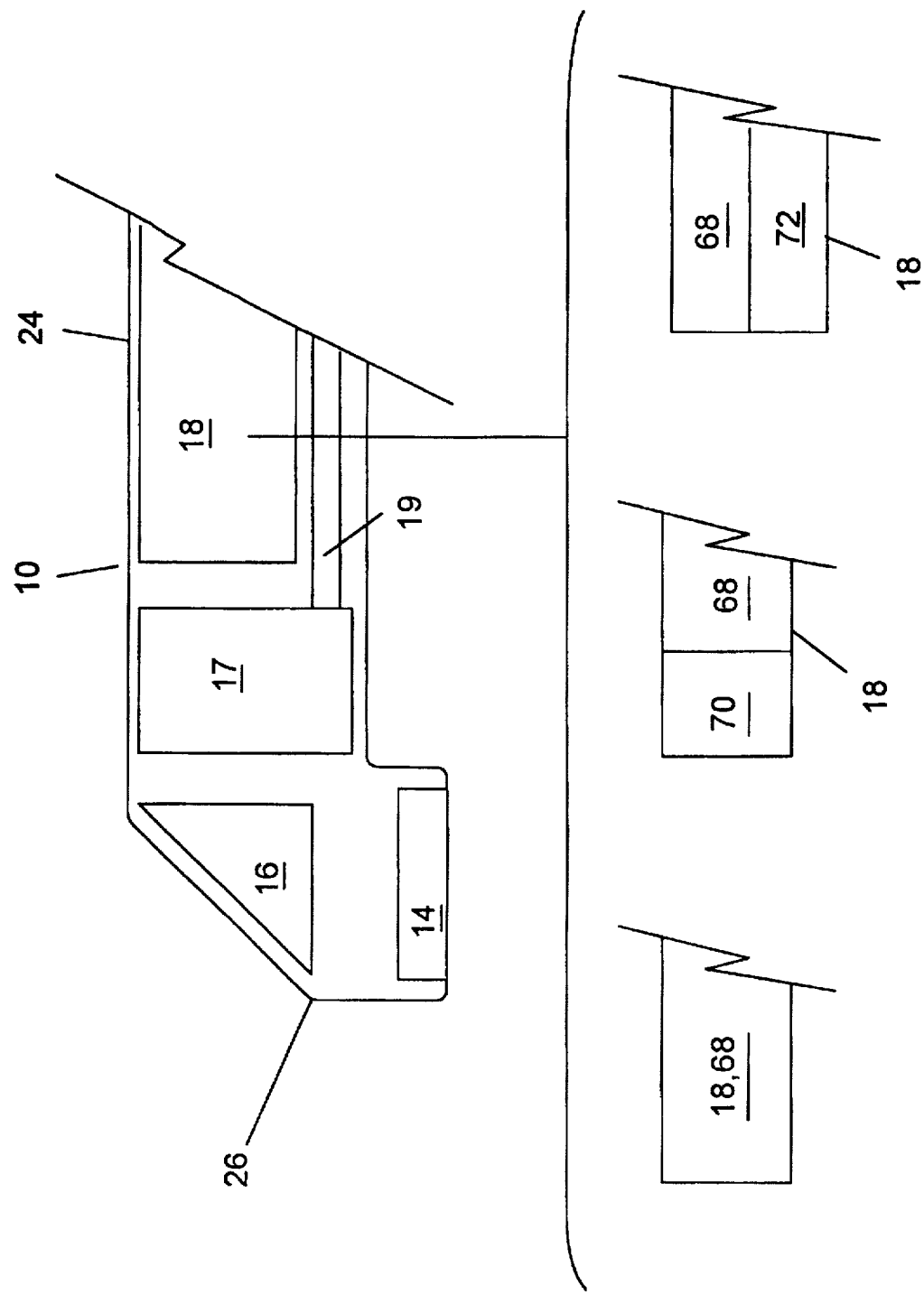

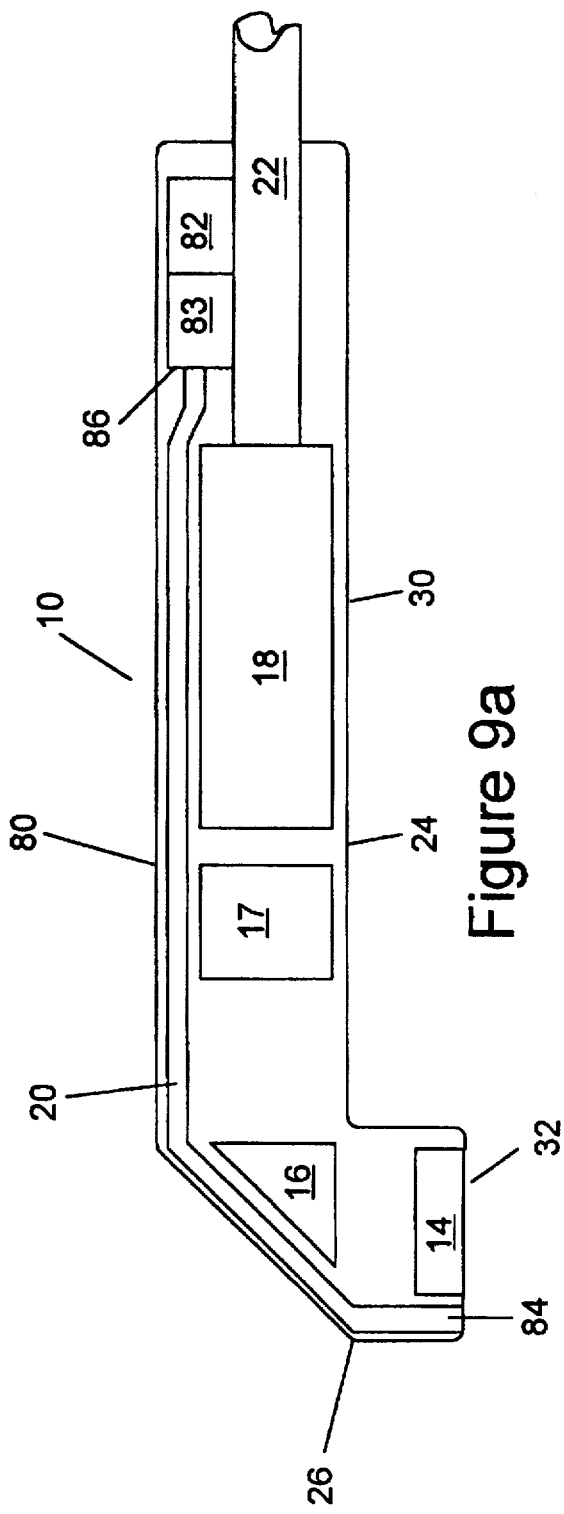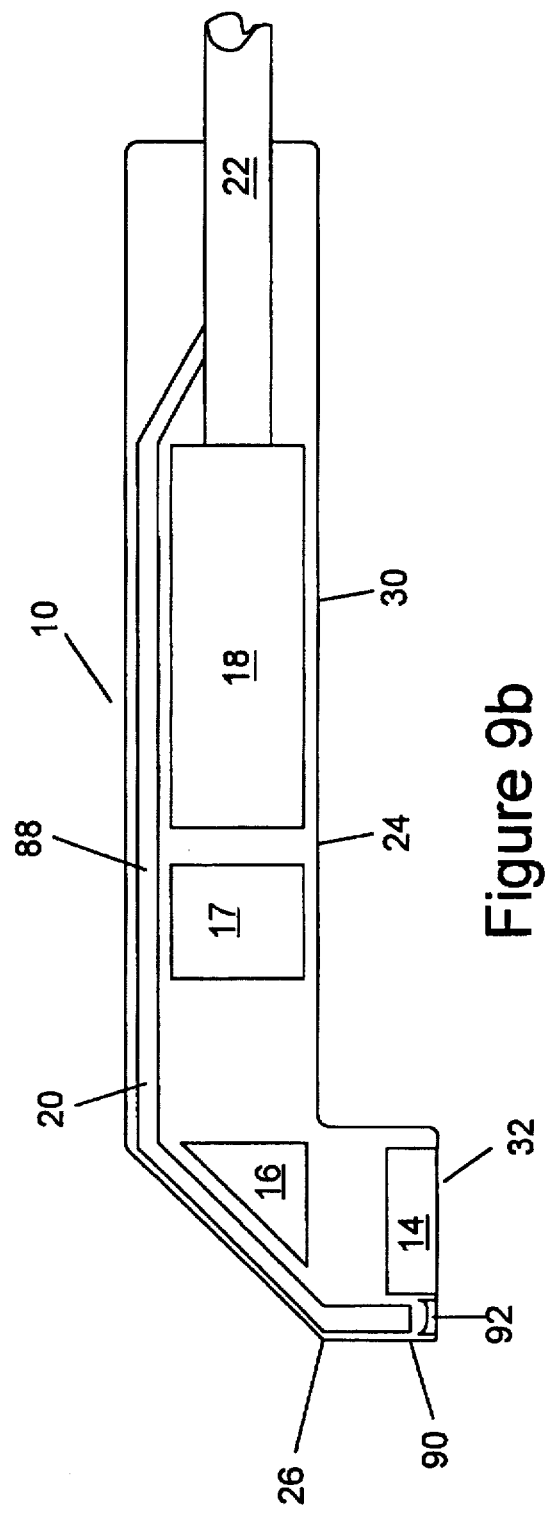

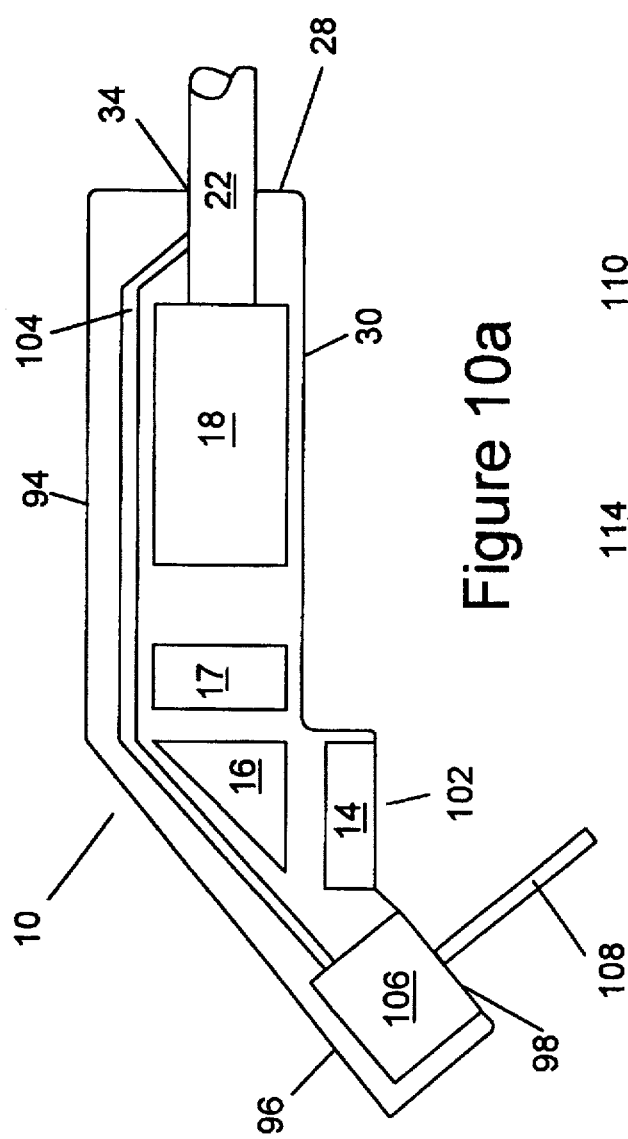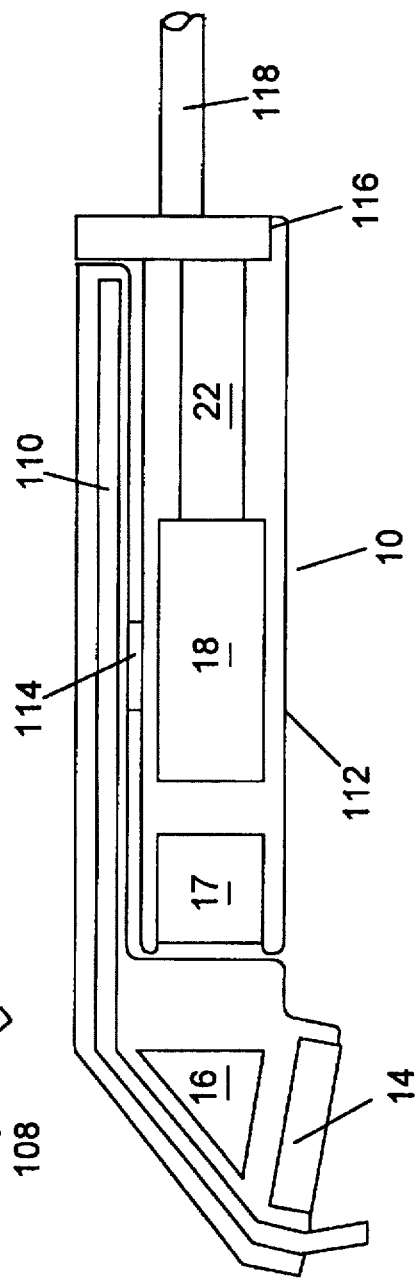

MODULAR INTRA-ORAL IMAGING SYSTEM VIDEO CAMERA

TECHNICAL FIELD

The present invention relates generally to imaging systems used in dentistry, and more particularly to intra-oral video cameras for such systems.

BACKGROUND ART

Practitioners of dentistry have long sought better ways to view surfaces inside the human mouth. Some dental surfaces are readily viewed by the unaided human eye. Others, however, require side or even retroflex directions of view which are difficult or impossible without optical aids.

One of the first, and today still most widely used, aids for viewing dental surfaces is the dental mirror. Unfortunately, such mirrors have numerous disadvantages. The image they provide is rotated (i.e., "mirrored" orientation), has fixed resolution, has a limited angle of view (also called field of view) and is generally too small to be viewed by more than one dentist at a time. Use of dental mirrors is not practical for direct viewing by the patient, or for use by the dentist to educate the patient. Dental mirrors can be separate devices, or they can be integrated into other dental instruments. However, when separate, a dental mirror usually requires that a separate hand be dedicated to holding it, and when integrated into another dental tool the mirror angle of view limitations may constrain the ability to perform other functions of the tool.

A modern improvement over the dental mirror is the endoscope. Endoscopes have found wide use in general medicine, as well as in other fields. They generally use a miniature image sensor, or combine a flexible fiber optic guide and an image sensor to transmit an image to a monitor. However, general endoscopes have limited use in dentistry. For example, most endoscopes have a tubular shape and are capable of only a zero-degree direction of view (i.e., out the axis or the end of the tube), which does not facilitate viewing of the distal portions of teeth. The Modular Endoscopic Apparatus With Image Rotation of U.S. Pat. No. B1 4,858,001, issued to Milbank, is an example of a prior art endoscope adapted for dental use which offers several advantages over prior art dental mirrors and endoscopes. Unfortunately, Milbank does not provide angles of view wide enough for all dental viewing needs, since it provides no angle of view enhancing optics and it redirects the image it captures with an inherently angle of view limiting mirror. And, the mirror reflector of Milbank also changes the image orientation.

Another improvement in the art of intra-oral imaging has been systems using fiber optic image guides permanently physically formed into shapes suitable for viewing in directions away from the major axis of the device. An examples of this is U.S. Pat. No. 5,049,070, issued to Ademovic.

Unfortunately, while significantly advancing the art of dental imaging, fiber optic guide based systems suffer from the relatively high cost of guides having suitable image transmission qualities, as well as physical radius of bend constraints for the fibers, when used for viewing in directions away from the major axis of the device.

To overcome the limitations of prior art dental mirrors, endoscopes, and other fiber optic guide instruments two additional types of intra-oral imaging systems have emerged, which the industry has termed direct and indirect intra-oral video camera ("IOVC") systems.

Direct IOVCs use image manipulating optics to obtain and process an image, then focus it directly onto a miniature charge-coupled device ("CCD") image sensor. FIG. 1 (prior art) is an illustration of a direct IOVC. Examples of direct IOVCs include U.S. Pat. Nos. B1 4,727,416; 5,016,098; 5,051,823; 5,251,025; and 5,290,168, all issued to Cooper. Direct IOVCs are constructed with the image manipulating optics (e.g., lenses or filters) and the image sensor all located in the end inserted into the patient's mouth; in dental terminology, the distal end of the device. Thus, the camera within a direct IOVC is introduced into a patient's mouth making it truly intra-oral in use, and the dimensions of the human mouth define its upper dimensional limits. Cooper '416 provides an example of a typical prior art direct IOVC. This device intentionally mimics the shape of dental mirrors, which has proven effective and which most dentists have grown accustomed to. But, where the reflective portion of a dental mirror is placed the Cooper '416 device substitutes manipulating optics and an image sensor, which even with todays miniaturization technology is much thicker than a simple mirrored surface. Components small enough for constructing such direct IOVCs today have very limited features and are more expensive. Thus, they are not capable of containing advanced features such as zoom lens systems, anything beyond the simplest of focusing systems, complex filters, or motorized automatic controls for such features. Direct IOVCs do, however, have particularly noteworthy advantages. Due to their simple lens-sensor construction they are capable of wide angles of view, higher resolution, and greater depth of focus. This simplicity is in marked contrast to other designs which use fiber optics, relay lenses, or rod lenses.

Indirect IOVCs, of which FIG. 2 (prior art) shows an example, add image relaying optics between the image capturing-reflecting optics and the image sensor to accomplish an additional degree of physical separation. The point of this physical separation is to permit mounting of the camera in the handle of the device. Thus, indirect IOVCs never actually introduce the camera itself into the patient's mouth, and their name is thus perhaps a misnomer. U.S. Pat. No. 5,124,797, issued to Williams, is an example that teaches the use of such relaying optics. By the use of relaying optics, the distal end of an indirect IOVC need only contain enough image manipulating optics, and, if designed for side or retroflex viewing, an image redirecting means like a reflector (see, e.g., FIG. 2 (prior art)) to pass a captured image out of the distal end and into the handle portion of the device. Since the image sensor is mounted in the handle of an indirect IOVC it does not necessarily have to be small enough to easily fit into the human mouth. And, as implied above, larger image sensors are generally readily available and less costly. Further, it is even possible in constructing indirect IOVCs to include zoom lenses and to use image sensor assemblies which include focusing systems, filters, and motorized automatic controls for these features. However, no indirect IOVCs known to the inventor currently provide such features. Indirect IOVCs unfortunately have an inherent disadvantage, due to the use of relaying optics they have added complexity, narrowed angle of view, limited resolution, and reduced depth of focus. Finally, a key point to be noted here is that, except for zero-degree viewing, indirect IOVCs require the use of a reflecting means such as a mirror or prism.

A disadvantage of mirrors and prisms is that they limit the angle of view, and once so limited, nothing can be done with additional optics to regain what has been lost. The maximum angle of view is typically 60 degrees or less when a mirror or prism is used as the first component in IOVC optics designed for a direction of view 90 degrees away from the major axis of the device. And for retroflex viewing directions (i.e., beyond 90 degrees) the angle of view becomes even more narrow. The severity of this restriction is further affected by the f/number of the entire optical system and the sensitivity of the image sensor, both of which are notably expensive features to improve upon.

Angle of view is an important criteria for an intra-oral imaging system. To view dental quadrants or the full dental arch from within the oral cavity, an angle of view of 90 degrees or more is desirable. In contrast, to view a single tooth during a dental procedure a narrower angle of view is preferred. And, effects related to the angle of view may also be important to the user. For example, when working on a single tooth, the inherent image distortion effect of a wide angle of view may be distracting. Whereas, with a narrow angle of view the need to "pan" across an area not fully encompassed in a single view may be tedious. Further, a narrow angle of view tends to amplify body motion as well as to reduce the depth of focus. And, when the depth of focus is too small the natural body motion of an IOVC operator may bring the viewed surface into and out of focus, or may fatigue the operator from excessive effort steadying the device. Thus in the field of dentistry a range of angles of view are needed which are tailored to the tasks being performed.

A further concern is that optical systems utilizing mirrors and simple prisms rotate or invert the orientation of an image, thus confusing viewers. So common is this that some experienced dentists, when given a choice, prefer instruments that mimic the false orientation which they have grown used to in dental mirrors. Correction of this effect is possible by electronic means, such as reversing the scanning circuits in the monitor, but doing so adds to the overall complexity of the imaging system. Further, if image inverting or rotating IOVCs are to be used on the same imaging system as non-inverting or non-rotating IOVCs, because of user preference or technical limitations, the system needs to provide selective correction, adding still more complexity.

Thus there is a present need in the art for an intra-oral imaging system capable of wide angles of view, capable of viewing in directions away from the major axis of the device (at least side viewing at right angle directions, and preferably in retroflex directions as well), but which does not itself necessarily change the image orientation from that which an unaided viewer would experience. Such a system should as much as possible still be capable of providing the desirable features of prior art dental viewing systems. Some examples of such features being user-familiar shape, ability to magnify, changeable point of focus, sufficient depth of focus for easy and non-fatiguing use, illumination providing ability, modular configuration ability, integration capability with other dental tools, modular integration with other dental tools, insensitivity to laser radiation, and easy cleaning as well as sterilization with typical techniques used in the medical fields such as autoclaving and chemical submersion.

DISCLOSURE OF INVENTION

Accordingly, it is an object of the present invention to provide an improved system for use in dental examinations, observing dental treatments, and facilitating the use of other dental tools to accomplish such treatments.

It is another object of the invention is to provide broad flexibility in configuring viewing capabilities with other dental operations.

Yet another object of the invention to provide a system for multiple viewers to observe dental examinations and treatments. Multiple viewers could concurrently perform an examination for diagnosis, or observe treatment for educational purposes. Viewing could occur at the site of the patient, or via conventional telecommunications distant from the patient. By the use of conventional video recording techniques, viewing could occur as the dental procedure progresses or at a later time. Thus also providing a system for taking visual records of dental conditions and dental treatments.

A further object of the invention is to provide a system to display intra-oral surfaces to patients. Patients could be better educated about many facets of dentistry. For example, patients could observe their own dental condition, and appreciate its gravity; they could give a more informed consent to a proposed dental treatment; or they could appreciate how to improve their own oral hygiene.

And, it is also an object of the invention to provide a viewing system for which the patient-contacting portions may be disposable, or easily cleaned and sterilized by typical medical techniques. The invention thereby provides a system for which sensitive components need not be exposed to the harsh rigors of such treatment, because they do not come into contact with either the patient or the operator.

Briefly, a preferred embodiment of the present invention is a modular form of direct IOVC for use in intra-oral imaging systems, to accomplish viewing in directions away from the major axis of the device. Optically, the IOVC includes an illumination provider, an angle of view enhancing objective, a non-image-inverting non-image-rotating reflector, a main image manipulating lens, and an image sensor assembly. In principle of operation, the illumination provider shines light onto the viewing area of the objective; the objective captures an image and projects it into the reflector; the reflector changes the direction the image travels and projects it into the main lens; and, the main lens manipulates the image into a desired form and then projects it onto the sensor assembly. Mechanically, the IOVCs modular form includes a frame interior module, and a sheath like sleeve exterior module. The frame holds the optical components of the device in suitable spatial alignment. The sleeve has defined therein a distal end, including a transparent window, and a handle portion. When the IOVC is assembled, the distal end becomes that portion most frequently contacting a patient, and the handle becomes that portion most frequently contacting an operator. Assembled, the window aligns with the illuminator and the objective, to permit light to reach the area to be viewed, and to allow images to reach the objective. Further, when assembled, the sleeve hermetically seals to the frame, thus providing barrier protection for the components mounted in the frame.

An advantage of the present invention is that wide angles of view of the imaged surface may be accomplished, despite viewing directions substantially away from the major axis of the invention.

Another advantage of the present invention is that greater depth of focus of the imaged surface may be accomplished, again despite viewing directions substantially away from its major axis.

And another advantage of the invention is that it can be implemented in a manner which provides non-inverted and non-rotated images to the viewer, also while providing viewing directions substantially away from its major axis.

Yet another advantage of the invention is that it may have integrated into it a system to illuminate the area viewed by the invention.

Still another advantage of the present invention is that it may be implemented in a manner to provide adjustable angles of view, magnification, focus, optical sensitivity, optical filtration, and dispersion of illumination. And, such adjustments may be provided in set increments or across varying ranges. Further, combinations of such parameters may be preprogrammed and selectively enabled as a group, thus allowing an operator to chose from among various preset viewing parameter sets for standard viewing situations, or to override such preprogramming and to specify special viewing parameters for particular situations.

A further advantage of the invention is that it may be integrated with another dental tool. Such integration may be permanent, creating a single tool of enhanced function, or modular to changeably permit joining with a multiplicity of other dental tools, thereby enhancing each. Such modularity may be either with the invention being the dominant unit and having other tools modularly added to it, or with the invention being the subservient unit and it being the module added to another, dominant, dental tool.

And yet a further advantage of the invention is that its own implementation may be modular. Thus the invention can by removing, replacing or supplementing optical elements cover a broader range of viewing needs. Further, the invention can be implemented to modularly disassemble, to facilitate cleaning and sterilization. One example is implementation to provide barrier protection (also known as "bagging"), a technique used to avoid contamination of medical implements or their components. Since precisely aligned optical assemblies and CCDs, as used in IOVCs, do not well tolerate harsh chemicals or the high temperatures of autoclave sterilization, the invention permits implementation with a removable sleeve exterior which can be disposable, or which may be separately cleaned or sterilized.

And still a further advantage of the invention is that it may be implemented for durable use with dental lasers. Easy integration into the invention of a suitable filter is possible, to suppress laser energy absorption and to prevent component life expectancy from being unduly shortened.

These and other objects and advantages of the present invention will become clear to those skilled in the art in view of the description of the best presently known mode of carrying out the invention and the industrial applicability of the preferred embodiment as described herein and as illustrated in the several figures of the drawings.

BRIEF DESCRIPTION OF THE DRAWINGS

FIG. 4a and 4b are views of the distal end portion of a simplified form of the embodiment of FIG. 3 respectively depicting use of a single negative lens and a telephoto lens assembly as the objective element in the invention;

FIG. 5a and 5b are views, similar to those of FIG. 4, which depict objective assemblies capable of respectively removing and changing objectives within the invention;

FIG. 6a, 6b and 6c are views, similar to those of FIG. 4, which alternatively depict the use of a mirror, an obtuse-angle triangular prism, and an acute-angle roof prism as reflectors within the invention;

FIG. 8 is a view, similar to those of FIG. 4, which depicts suitable sensor assemblies based on a charge coupled device ("CCD"), as well as possible filter and focusing options;

FIG. 9a and 9b are views of the preferred embodiment which depict integration of a light guide into the invention, to provide viewing area illumination, with FIG. 9a showing use of a light guide utilizing a light source internal to the invention, and FIG. 9b showing use of a light guide utilizing an external light source, from which light is conveyed into the invention;

FIG. 10a depicts permanent integration of the invention with a dental drill, while FIG. 10b depicts a modular changeable integration of the invention with a dental laser;

BEST MODE FOR CARRYING OUT THE INVENTION

Figure 1:
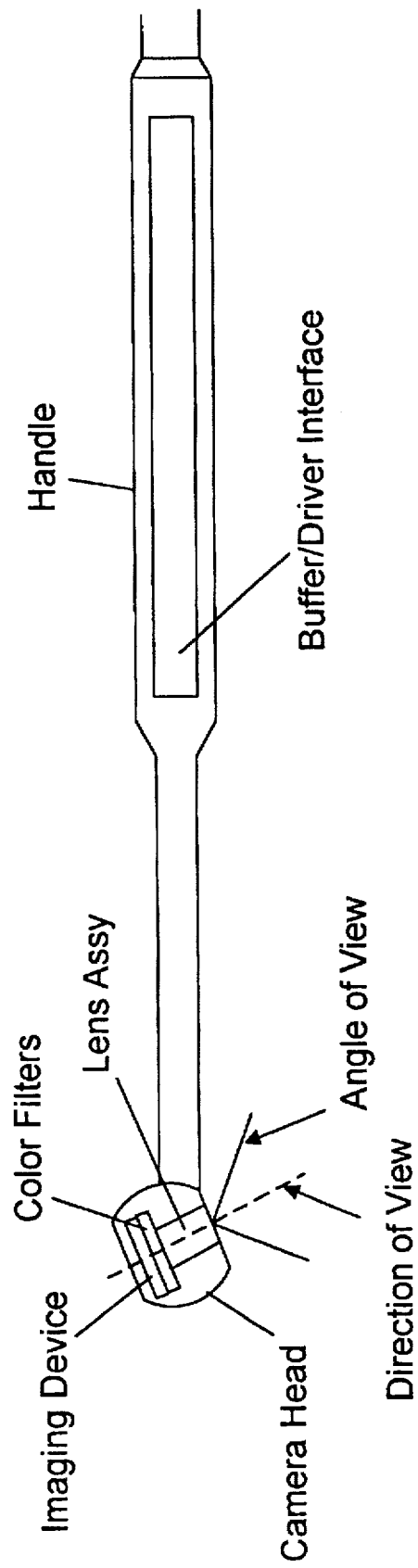
FIG. 1 (prior art) is a major axis cross sectional view of a typical prior art direct optical IOVC.
Figure 2:
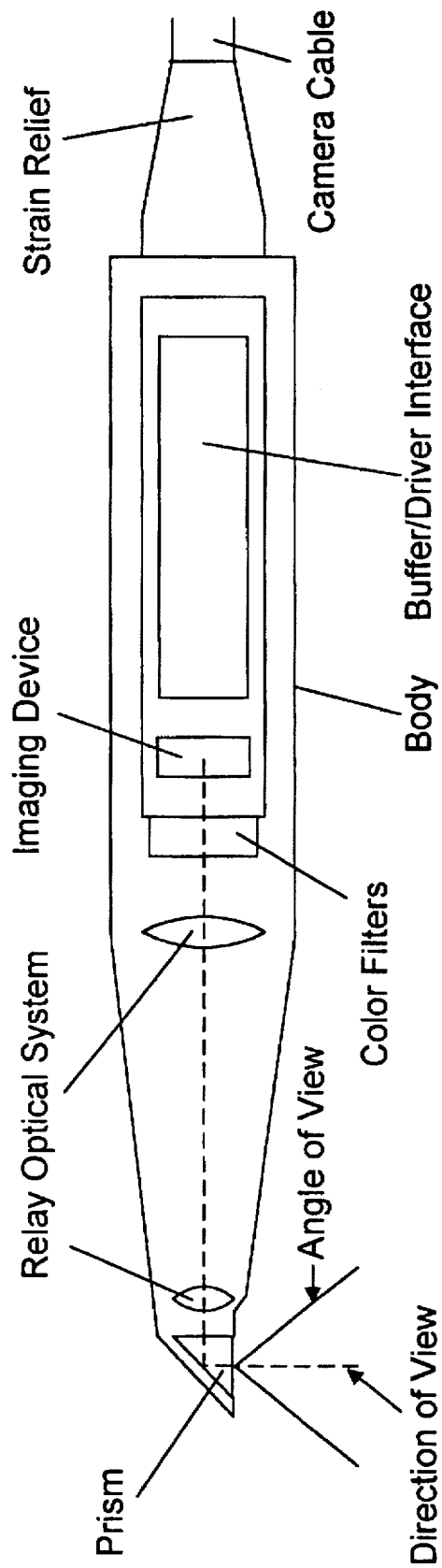
FIG. 2 (prior art) is a major axis cross sectional view of a typical prior art indirect optical IOVC.

The preferred embodiment of the present invention is a modular multipurpose direct optical intra-oral video camera ("IOVC") providing an image which is not inverted, is not rotated, has a wide angle of view, and which may be captured at a substantial direction of view away from the major axis of the device. As illustrated in the various drawings, and particularly in the view of FIG. 3, a basic form of the preferred embodiment of the invention is depicted by the general reference character 10.

The IOVC 10 is generally symmetrical about a major axis plane 12, which bisects it longitudinally. As illustrated in the various figures of the drawings, and particularly in the cross sectional view of FIG. 3, the IOVC 10 includes several separately described assemblies. These include an objective assembly 14; an objective conduit branch 15; a reflector 16; a main lens assembly 17; a main lens assembly conduit branch 19; a sensor assembly 18; an illumination assembly 20; a conduit system 22; and a housing 24, having defined therein a distal end 26, a proximal end 28, a handle portion 30, a view port 32, and a conduit port 34.

The Objective Assembly 14:

As shown in FIG. 4a and 4b (based on a simplified version of FIG. 3), the objective assembly 14 includes as a preferred feature a negative optical element 35, to broaden or controllably define the angle of view of the inventive IOVC 10. FIG. 4a shows a negative lens 36 being used alone as the negative optical element 35 portion of the objective assembly 14, to compensate for the inherent angle of view restriction caused by the reflector 16. FIG. 4b illustrates the use of a telephoto lens 38 for the objective assembly 14. High magnification with a controlled angle of view restriction is accomplished by inclusion of a negative lens element 40 as the negative optical element 35 within the telephoto lens 38, again to compensate for the angle of view restriction caused by the reflector 16.

Alternate embodiments of the objective assembly 14 permit selective disablement of the compensating effect, to provide a plurality of angle of view choices. FIG. 5a illustrates an objective assembly 14 including a remover subassembly 42 and a lens 44. An operator may controllably activate the remover subassembly 42 to withdraw the lens 44 from the optical path to the reflector 16, so that the lens 44 does not affect the inherent angle of view limiting effect of the reflector 16.

Similarly, other embodiments of the objective assembly 14 permit an operator to chose from among a plurality of lenses, to provide a plurality of selectable viewing characteristics. FIG. 5b illustrates an objective assembly 14 which includes a front lens 48a and a rear lens 48b held by a transfer unit 50. When an operator activates the transfer unit 50 to put the front lens 48a into the optical path to the reflector 16 the transfer unit 50 also moves the rear lens 48b into a rear storage location 52b. And, similarly, as actually illustrated in FIG. 5b, when the operator activates the transfer unit 50 to place the rear lens 48b into the optical path to the reflector 16 the transfer unit 50 also moves the front lens 48a into a front storage location 52a. Typically, front lens 48a and rear lens 48b would be chosen to have significantly different optical characteristics, and thus permit selectively viewing a wide area like a dental arch or a magnified narrower area such as that of a single tooth. It is to be noted that FIG. 5b shows features for illustration, which are not to be construed as limiting. While only two lenses are shown, other pluralities are easily possible. Similarly, while operation in a slidable manner is shown, other means for selecting from a plurality of lens are also suitable, one example of which would be a rotating turret. And, operator control of the transfer unit 50 may be by various means as are well known for the general art of hand held tools. Examples of which include positive manual operation, electrical micro-motor operation, pneumatic operation, and hydraulic operation.

If desired, remote control signals for the transfer unit 50, the remover subassembly 42, and other options within the objective assembly 14 may be provided by an optional objective conduit branch 15, described further below with the conduit system 22.

The objective assembly 14 is an optional component of the inventive IOVC 10. However, it is anticipated that in most embodiments of the invention it will be desirable, particularly when the negative optical element 35 is include, to enhance or controllably define the angle of view of the IOVC 10.

The Reflector 16:

This component provides the inventive IOVC 10 with the ability to view dental surfaces in directions of view substantially away from the major axis plane 12.

FIG. 6a shows the use of a mirror 54, as the reflector 16, to accept an image from the objective assembly 14, redirect that image (90 degrees), and project the image into the main lens assembly 17. FIG. 6b shows the use of an obtuse-angle triangular prism 56 as the reflector 16, to similarly accept, redirect (103 degrees), and project an image. And, FIG. 6c shows the use of an acute-angle roof prism 58 as the reflector 16, to again accept, redirect (82 degrees), and project an image.

The use of the roof prism 58 in FIG. 6c deserves particular emphasis as a preferred embodiment of the inventive IOVC 10 because, unlike mirrors and simpler types of prisms which invert or "rotate" the image itself (the "mirror image" effect), roof prisms as a class do not affect the orientation of visual data within images as they change the direction in which images travels. It should be noted with particularity, the subtle semantic distinction between rotation of the orientation of an image (i.e., mirror imaging) and rotation of the direction (i.e., redirection) in which an image is projected.

Figure 11:
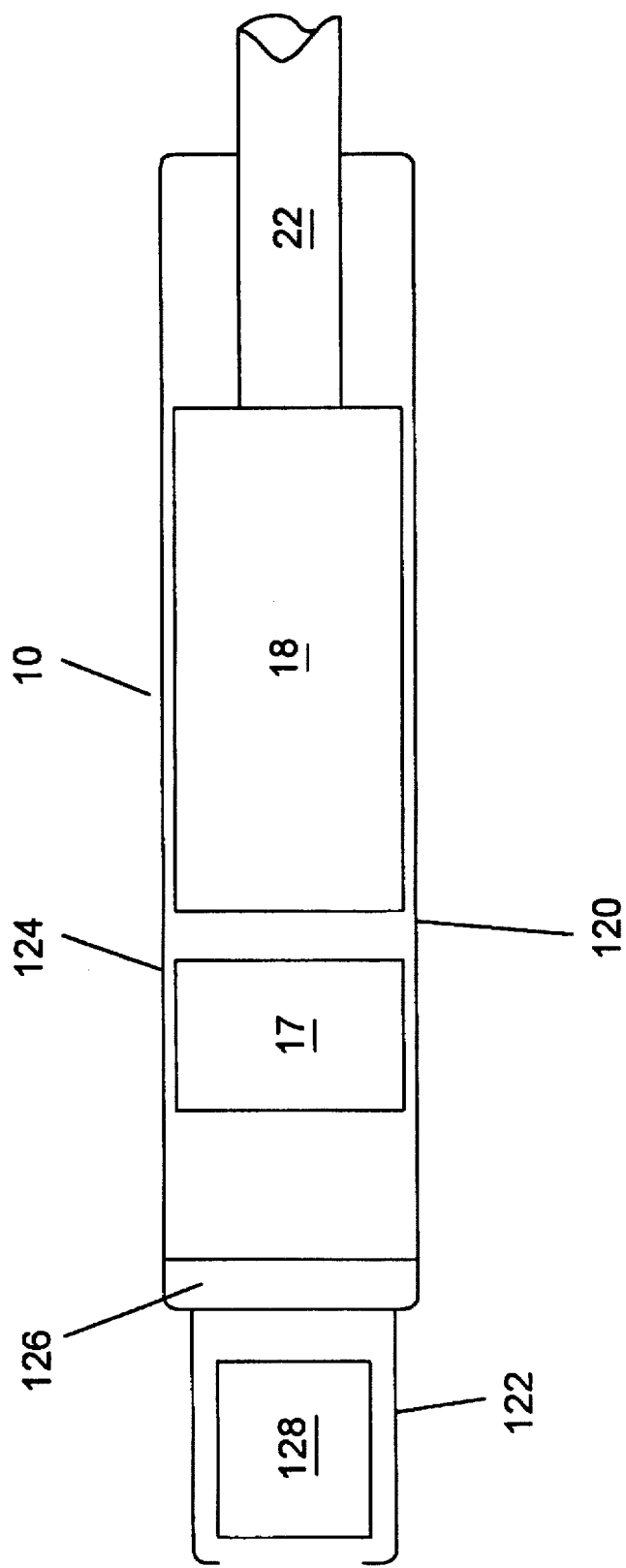
FIG. 11 depicts a modular implementation of the invention, with a zero-degree viewing end module mounted.

In principle, the reflector 16 is optional. However, omission of the reflector 16 limits the direction of view of the IOVC 10 to zero-degree viewing. An example of such an implementation is shown in FIG. 11, which is discussed further below. In practice, due to the shape of the human mouth and the need for side viewing capability, therefore, it is anticipated that most embodiments of the IOVC 10 will include this component.

The Main Lens Assembly 17:

The main optical manipulations upon images captured by the IOVC 10 are performed by the main lens assembly 17. Unlike prior art IOVCs where only a single lens component was possible (see, e.g., FIG. 1 (prior art)), the inventive design of IOVC 10 permits use of two lenses, the objective assembly 14 (discussed above) and the main lens assembly 17. Both of these lens components are optional. However, in most embodiments of the inventive IOVC 10 both will be desired. The benefits of the objective assembly have been discussed above.

The key benefit from inclusion of the main lens assembly 17 is a considerable reduction in the size of the objective assembly 14. As can be appreciated from FIG. 3, since the size of the objective assembly 14 is a factor in the dimensions of the distal end 26 of the IOVC 10, and the distal end 26 must enter into a patient's mouth, it follows that reducing the size of the objective assembly 14 is desirable. Such a reduction is possible by a division and allocation of labors. By using both an objective assembly 14 and a main lens assembly 17, together the only necessary duty of the objective assembly 14 becomes angle of view preservation, and thus it need only be large enough for that purpose. Other image manipulation duties, and any necessary increased component size to accomplish them, can be relegated to the main lens assembly 17. In a side direction viewing embodiment, such as FIG. 3, this becomes effectively a trade of critical distal end 26 thickness of the housing 24 for less critical distal end 26 length.

Figure 7:
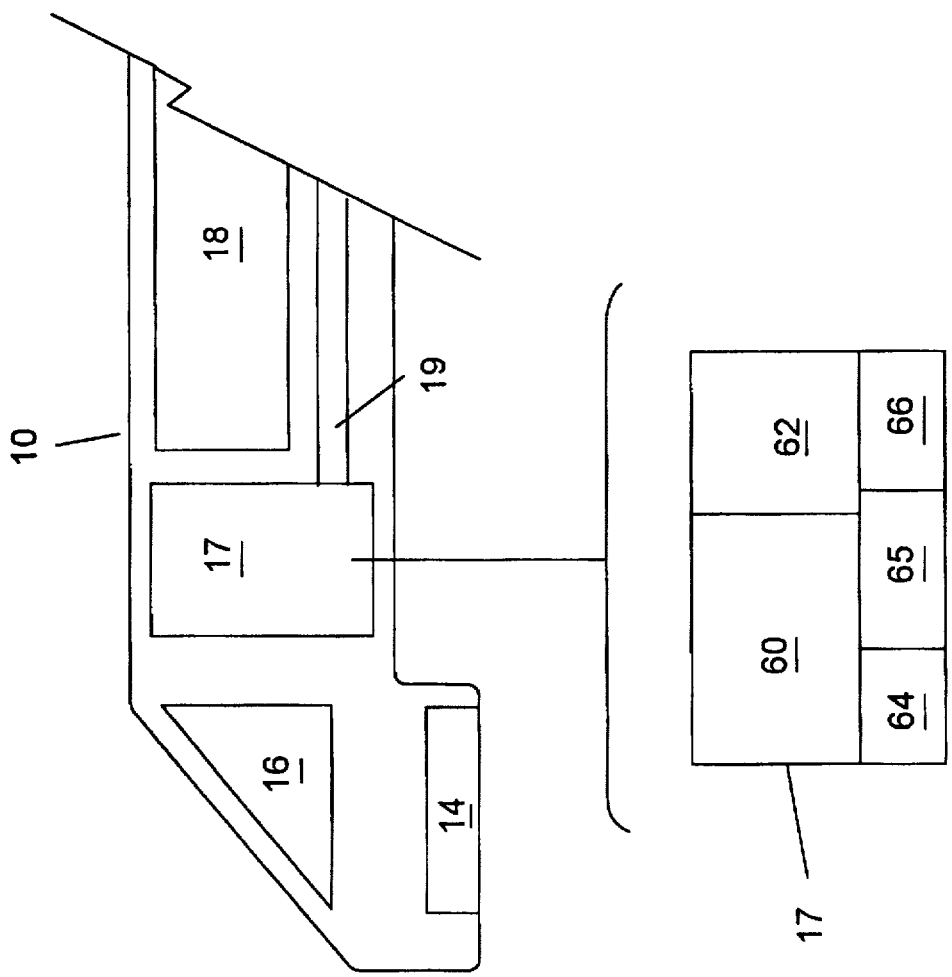
FIG. 7 is a view, similar to those of FIG. 4, which depicts an optional main lens assembly, as well as possible aperture, zoom capability, and focusing options.

FIG. 7 illustrates three optional features within the main lens assembly 17 an aperture 60, a zoom lens 62, and a focus adjuster 65. Because such options generally take up space, their inclusion in prior art direct IOVCs has been impractical. When the aperture 60 is provided the main lens assembly 17 may also include an aperture adjuster 64, such as, for example, an iris diaphragm. Similarly, when the zoom lens 62 is provided the main lens assembly 17 will include a zoom adjuster 66. The focus adjuster 65, if provided, operates by principles well known in the art of optics. Examples of which include changing the internal optical characteristics of the main lens assembly 17, and moving the main lens assembly 17 as a whole relative to the other optical components (i.e., relative to the reflector 16 and the sensor assembly 18). Operator control of the aperture adjuster 64, the zoom adjuster 66, and the focus adjuster 65 may be by any of mechanisms well known for the general art of hand held tools, examples of which have previously been noted.

If desired, remote control signals for the aperture adjuster 64, the focus adjuster 65, the zoom adjuster 66, and other options within the main lens assembly 17 may be provided by an optional main lens conduit branch 19, described further below with the conduit system 22.

While shown here in a preferred location, within the IOVC 10, which is consistent with generally accepted optical system design practice and availability of commercial units, it is to be noted that these features could also be placed in other locations. For example, the aperture 60 and its attendant aperture adjuster 64 could be made part of the objective assembly 14, or be placed between the objective assembly 14 and the reflector 16. Similarly, the zoom lens 62 and its attendant zoom adjuster 66 could also be made part of the objective assembly 14, or be integrated into the sensor assembly 18. The function of the focus adjuster 65 may also be performed at another location in the IOVC 10, one example of which is discussed below with the sensor assembly 18.

The Sensor Assembly 18:

It is a key aspect of the inventive IOVC 10 that this component is placed in the distal end 26 of the housing 24. In this manner the need for relaying optics, which would made the device an indirect IOVC, is avoided, along with their inherent disadvantages. And, by using the reflector 16, for side direction viewing, the thickness constraints on equivalent components in prior art side viewing direct IOVCS are also avoided. Thus, the dimensional constraints for this component are lessened by the improved direct optical nature of the inventive IOVC 10, and a large range of commercially available and full featured image sensors of the charge coupled device ("CCD") type may be used. Typical commercially available and acceptable CCDs today have diameters of one-third to one-quarter inch, and smaller units are anticipated to become available. Thus, the inventive IOVC 10 may be constructed with dimensions roughly equivalent to those of other commonly hand held utensils, e.g., ink pens.

FIG. 8 illustrates some embodiments utilizing a few of the numerous commercially available features for sensor assembly 18. A CCD 68 may be used alone, or optional features may be included such as a filter 70, a focusing unit 72, or both (not shown). The filter 70, while optional, may be desirable, for example, to modify the image captured by the CCD 68, or to protect it from stray emissions when a laser dental tool is being used. When the focusing trait 72 is provided here its principle of operation is to reposition the CCD 68 relative to the main lens assembly 17, which can be accomplished by the use of mechanisms well known for the general art of hand held tools, examples of which have previously been noted.

The Illumination Assembly 20:

FIG. 9a displays an embodiment in which the illumination assembly 20 includes a light guide 80 and a light source 82, both located entirely inside the IOVC 10. The light guide 80 has a terminal end 84, located at the view port 32 in the distal end 26 of the housing 24, and a source end 86. In FIG. 9a an optional light dispersion element 83 is shown placed on the source end 86 of the light guide 80. The principle of operation for the dispersion element 83 here is based on the characteristic of light guides that light suitably introduced into a guide, either by a separate optical element or by shaping the receiving optical surface of the guide, affects the dispersion of the light that exits the guide. Therefore, in operation of the illumination assembly 20 as a whole, light emitted by the light source 82 is captured by the dispersion element 83 at the source end 86 of the light guide 80 and communicated to the terminal end 84 of the light guide 80, where it exits and shines out the view port 32 to illuminate the viewing area of the IOVC 10. Power for the light source 82 is communicated into the IOVC 10 as one of the utilities carried by the conduit system 22 (discussed below).

FIG. 9b illustrates an embodiment in which the illumination assembly 20 includes a light guide 88 that extends into the IOVC 10 as an integral part of the conduit system 22, from a light source (not shown) located outside of the IOVC 10. Here also, the light guide 88 has a terminal end 90, located at the view port 32 in the distal end 26 of the housing 24. An optional light dispersion element 92 is shown, placed at the terminal end 90 of the light guide 88. Operation for the dispersion element 92 here is based on the conventional optical index of refraction principle that either a separate optical element or a suitable optical surface affects the angle (i.e., dispersion) of the light passing through it. Operation of the illumination assembly 20 as a whole here, in principle, is the same as that described above for FIG. 9a.

While the dispersion element 83 of FIG. 9a and dispersion element 92 of FIG. 9b have above been treated as single elements, there is no reason why they could not instead be dispersion assemblies, including multiple dispersion elements with capability for selection among individual dispersion elements. For example, referring back to FIG. 5a and 5b, the inventive IOVC 10 illustrated there is capable of different operator selectable angles of view. It is anticipated that the angle of view provided by the front lens 48a will be different than that provided by the rear lens 48b. Therefore, it follows that different fields of illumination may be desirable, which a dispersion assembly can provide. Further, since the angle of view of the IOVC 10 and the field of dispersion of the illumination assembly 20 have a fixed relationship, it is advantageous to combine any user selection mechanism for changing them.

Finally, the dispersion element 83 of FIG. 9a and the dispersion element 92 of FIG. 9b are optional. However, due to the wide angle of view characteristics of the inventive IOVC 10 it is anticipated that either one, or even both of these options in combination, will be desirable to insure that the entire image area viewed by the IOVC 10 is sufficiently illuminated. Further, while only one illumination assembly 20 has been shown here, typical embodiments of the IOVC 10 may use multiple assemblies. For example, to provide more uniform distribution of light across the entire field of illumination, or to soften shadow effects.

Figure 3:
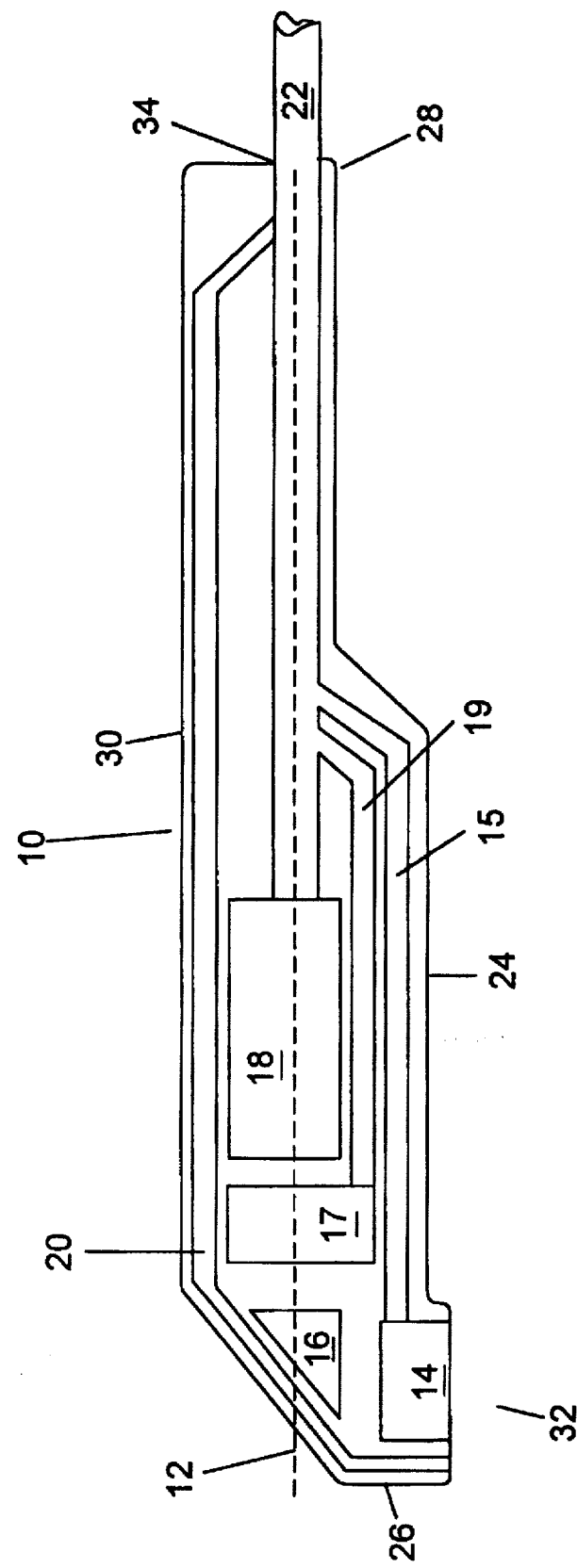
FIG. 3 is a major axis cross sectional view of a deluxe version of an IOVC constructed in accordance with the teachings of this invention.

The Conduit System 22:

As shown in FIG. 3, the conduit system 22 communicates the utility needs of the inventive IOVC 10. And, as shown in FIG. 10a–b, it also communicates any utility needs of a dental tool integrated with the inventive IOVC 10. Such utilities typically will include power and control signals for the sensor assembly 18 and options in the objective assembly 14 and the main lens assembly 17, as well as image data signals out of the sensor assembly 18, to a monitoring system (not shown). In embodiments like those of FIG. 5a–b, any optional features for which remote control capability is provided, the utility needs of those features are also communicated into the IOVC 10 first via the conduit system 22 then via the objective conduit branch 15. In embodiments like that of FIG. 7, where optional features such as an aperture 60 with an aperture adjuster 64, a zoom lens 62 with a zoom adjuster 66, or a focus adjuster 65 are provided, the utility needs of the features are also communicated into the IOVC 10 first via the conduit system 22 then via the main lens assembly conduit branch 19. Similarly, in FIG. 9a, where the light source 82 needs power, and in FIG. 9b, where the illumination assembly 20 needs light energy from outside of the IOVC 10 these utility needs are also communicated by the conduit system 22.

Since the conduit system 22 may be connected to all operator controllable components within the IOVC 10 (e.g., the objective assembly 14, the main lens assembly 17, the sensor assembly 18, and the illumination assembly 20) it should be appreciated that coordinated operation and pre-programmed setting options of these components may be provided. Thus an operator can be relieved of the need to individually set each component when a standard viewing situation is desired. An operator need only select a general mode of viewing desired (e.g., single tooth surface, or full dental arch) and all specific settings can be automatically made, including, for example, angle of view, magnification, focus, aperture, and illumination intensity.

The Housing 24:

As can be seen in FIG. 3, the housing 24 holds all of the components of the invention in suitable spatial relationship. In the general manner for designating parts of dental implements, the housing 24 has defined therein a distal end 26, which is that end inserted into a patient's mouth, and a proximal end 28, which is that end opposite the distal end 26. Further, the distal end 26 has suitably located therein a view port 32, through which an image reaches the objective assembly 14. The proximal end 28 has therein a conduit port 34, through which the conduit system 22 enters the IOVC 10. Further, the housing 24 has defined thereon a handle portion 30, suitably formed for grasping of the IOVC 10 in the hand of an operator.

Suitable variation in housing design permits considerable variation in the usefulness of the inventive IOVC 10. For example, FIG. 10a illustrates an embodiment where the inventive IOVC 10 is permanently integrated with another dental tool. A modified housing 94 is provided, having an enlarged distal end 96 which includes a tool port 98 and a view port 102. The proximal end 28, the handle portion 30, and the conduit port 34 remain the same as those disclosed in FIG. 3. Further included are a conduit subsystem 104, and a dental drill 106 which has an operating extremity 108. The dental drill 106 is contained in the distal end 96 of the housing 94, while the operating extremity 108 of the dental drill 106 extends out of the IOVC 10 through the tool port 98. The conduit subsystem 104 extends from the dental drill 106 in the distal end 96, through the handle portion 30 of the housing 94, and joins with conduit system 22 before it exits the IOVC 10. The conduit system 22, in addition to communicating the utility needs of the IOVC 10 itself, further communicates any utility needs of the dental drill 106, such as power, air, vacuum, and water. In operation, the operating extremity 108 of the dental drill 106 is used to perform work on a patient's dental surfaces, while the IOVC 10 is used to closely examine those dental surfaces and the progress of that work.

In an alternate variation of housing design, another dental tool may be modularly integrated with the inventive IOVC 10, either in a full or in a partial manner. FIG. 10b illustrates an example of such an embodiment, where a dental laser 110 in the form of a sub-module, containing some components which could have been included as options in the IOVC 10, is coupled with the inventive IOVC 10 in the form of a main module. The housing 112 of the IOVC 10 includes a clasp 114, suitable for temporarily holding the IOVC 10 and the dental laser 110 together so that they may effectively function as a single hand tool during use. In principle, since direction of view, which is controlled by the reflector 16, and the angle of view, which is controlled by the objective assembly 14, remain fixed when in use with a specialized tool it is logical to include those optional components in the sub-module tool. Further, such an allocation of optional components, with their respective functions, among the multiple modules is actually advantageous for purposes of sterilization and cleaning. For example, some components of the basic IOVC 10, such as the sensor assembly 18 including the sensitive CCD 68 (see, e.g., FIG. 8), can not tolerate the heat of autoclaving. Other, optional, components of the IOVC 10, such as the objective assembly 14 and the reflector 18 here, as well as the dental tool may be autoclaved. Therefore, hygienic standards can be maintained by "bagging" the IOVC 10 main module and portions of the dental tool module during use, and then autoclaving the sub-module tool alone.

While it should be noted that the IOVC 10 in such an integrated relationship with another dental tool could simply continue to use an entirely separate conduit system, FIG. 10b shows the use of a universal connector 116 to attach the conduit system 22 of the IOVC 10 to a master conduit system 118, which communicates the utility needs (e.g., laser energy, power or coolant) of the dental laser 110, and via the universal connector 116 and the conduit system 22, and also communicates the utility needs of the IOVC 10. While FIG. 10b illustrates a preferred embodiment where the IOVC 10 is the dominant tool and accepts and provides utility support to the subservient dental laser 110 module. It should be appreciated that the inventive IOVC 10 may also be implemented as the subservient tool, modularly attaching to and using the utility system of another dental tool.

In another housing design variation, the inventive IOVC 10 itself may be modularly implemented, for example, to facilitate reconfiguration. FIG. 11 illustrates such an embodiment for zero-degree viewing, having a modified housing 120 which includes a changeable end module 122 and a main body 124. The main body 124 includes a retainer 126, for attaching the end module 122. The end module 122 contains an alternate objective assembly 128, while the main body 124 contains the basic main lens assembly 17, basic sensor assembly 18, and basic conduit system 22 (previously discussed for FIG. 3). In function, the IOVC 10 is configured here to function much as a simple endoscope. It should be noted that a considerable variety of designs for alternate end modules are possible, without deviation from the spirit of the invention. For example, one variation is to use a mirror reflector (in principle, the same as the mirror 54 used in FIG. 6a), to accomplish side viewing, while in another variation an acute-angle roof prism reflector could be used (in principle, the same as the acute-angle roof prism 58 of FIG. 6c), to accomplish retroflex viewing.

Figure 12:
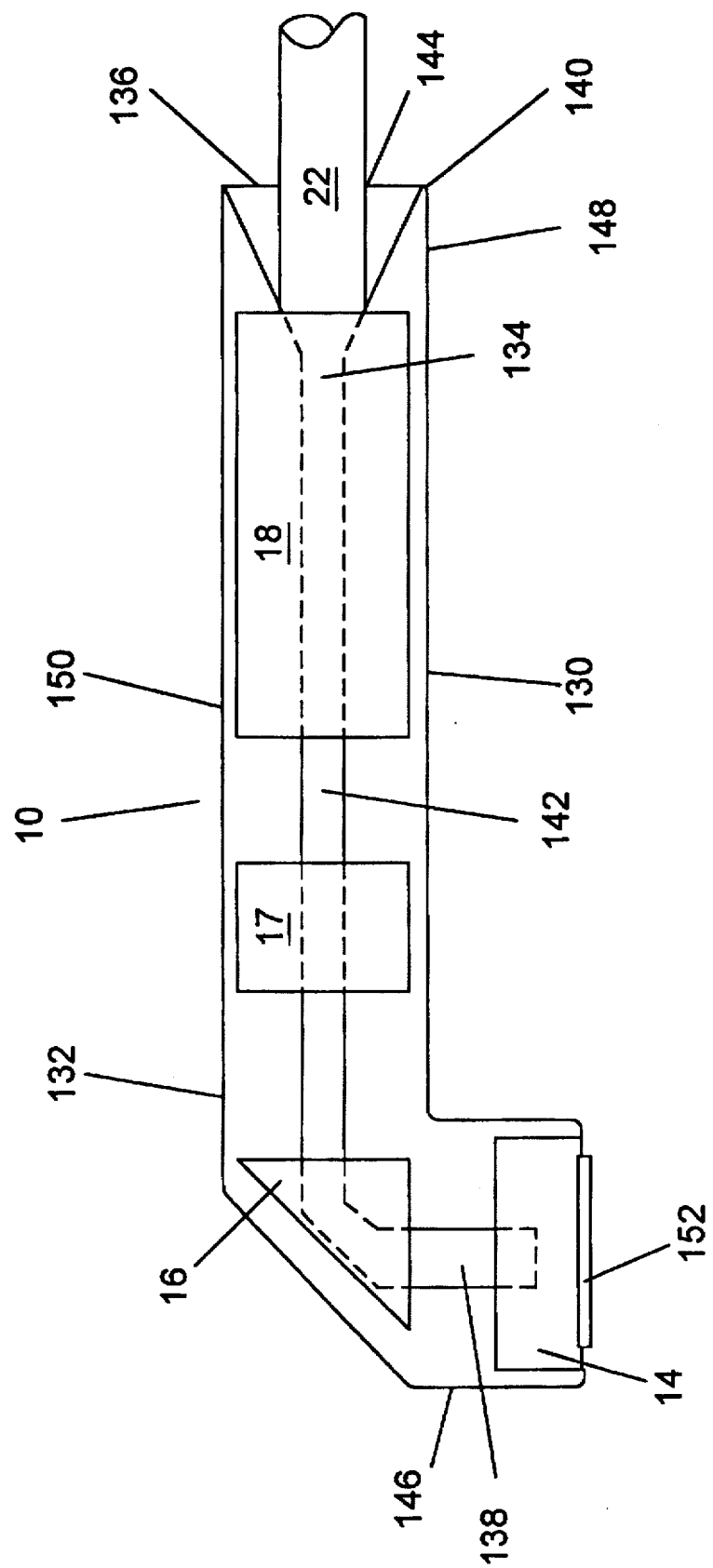
FIG. 12 depicts another modular implementation of the invention, where a sleeve module is the exterior of the invention, to facilitate cleaning and sterilization.

In another alternate housing design, cleaning and sterilization may be facilitated by including barrier protection for the optical and electrical components of the inventive IOVC 10. FIG. 12 illustrates such an embodiment, wherein a modified housing 130 includes a sleeve 132, a frame 134, and a sealer 136. The frame 134 is defined to have therein a distal end 138, a proximal end 140, a central portion 142, and a conduit port 144. Similarly, the sleeve 132 has defined therein a distal end 146, a proximal end 148, and a handle portion 150. The sleeve 132 has further defined therein a transparent window portion 152. The basic objective assembly 14, the basic reflector 16, the basic main lens assembly 17, the basic sensor assembly 18, and the basic conduit system 22 (as discussed for FIG. 3) remain the same in this embodiment, except that here they are held in suitable spatial relationship by the frame 134. When the sleeve 132 is installed over the frame 134, the proximal end 148 of the sleeve 132 and the proximal end 140 of the frame 134 suitably align and are hermetically sealed together by the sealer 136. And, when the sleeve 132 is installed, its window portion 152 aligns with the objective assembly 14 in a suitable manner to permit images to reach the objective assembly 14 through the window portion 152. Thus, the sleeve 132 becomes the main exterior of the IOVC 10, specifically it becomes the surface introduced into a patients mouth, as well as that held by an operator. Cleaning or sterilization concerns for the sleeve 132 itself can be addressed by making it disposable, or by making it of suitable materials to withstand submersion in chemicals or the heat of an autoclave.

In addition to the above mentioned examples, various other modifications and alterations of the IOVC 10 may be made without departing from the invention. Accordingly, the above disclosure is not to be considered as limiting and the appended claims are to be interpreted as encompassing the entire spirit and scope of the invention.

INDUSTRIAL APPLICABILITY

The intra-oral video camera ("IOVC") 10 according to the present invention is adapted for use in conventional dentistry as it is practiced today, as well as it is reasonably anticipated that it will continue to be practiced for some time. In this respect, the IOVC 10 may function as a tool for the examination and treatment of patients, or it may, through integration with another dental tool, function to enhance the utility of that other dental tool.

The IOVC 10 according to the present invention is also suitable for expanding the practice of dentistry in manners which have not previously been possible, or in manners which were impractical or difficult to accomplish with prior technology. The inventive IOVC 10 is particularly well suited for displaying dental surfaces to multiple viewers, either in a clinical, an educational, or another form of setting. Notably, the patient may themselves be one of these viewers. This is largely an unexploited capability in dentistry, which has only recently become practical with any form of dental examination system. Yet, this ability is one which the inventive IOVC 10 can easily perform. Further, such examination or observation can be either time or location displaced. Images captured by the IOVC 10 may, through the use of conventional video recording techniques, be preserved and viewed at a later time. Or, images captured by the IOVC 10 may, through the use of conventional televisual techniques, be viewed at remote or multiple locations.

For the above, and other, reasons it is expected that the IOVC 10 of the present invention will have widespread industrial applicability. The IOVC 10 may be constructed as a full featured camera device, yet be constructed small enough that it meets the dimensional constraints of the human mouth. The IOVC 10 also provides a substantial optical advantage because it does not necessarily affect image orientation, which may confuse viewers or add the burden of correction to monitoring equipment. Further, the IOVC 10 provides the additional optical advantage of being implementable in forms suitable for viewing in directions ranging from zero degrees (i.e., out its major axis) to the extreme retroflex. And, the IOVC 10 can accomplish such a range of viewing directions and a variety of viewing characteristics in an economic manner by the changing of only a small modular portion of the overall invention. Therefore, it is expected that the commercial utility of the present invention will be extensive and long lasting.

I claim:

1. A dental video camera for use in displaying images from inside a patient's mouth onto a monitor, comprising:
   a. a housing, having defined therein
      i. a handle portion, and
      ii. a distal end, which includes a view port;
   b. a sensor assembly, mounted in said distal end of the housing and optically aligned substantially along a longitudinal axis through said housing, for converting to data signals images which have entered the camera through said view port;
   c. a reflector located in the optical path to said sensor assembly and suitable for directing images from at least 90 degrees away from said longitudinal axis into said sensor assembly; and
   d. utility conveying means for conveying power and control signals into and data signals out of the camera.

2. The camera of claim 1, further including an objective lens assembly, located in the optical path to said sensor assembly, for suitably tailoring initial characteristics of images captured by the camera.

3. The camera of claim 2, wherein said objective lens assembly includes a negative lens, for controlling the camera angle of view.

4. The camera of claim 2, wherein said objective lens assembly includes removal means, to permit selectively removing said objective lens assembly from the optical path to the sensor assembly, to provide two viewing characteristic sets for the camera.

5. The camera of claim 2, wherein said objective lens assembly includes:
   a. a plurality of lenses; and
   b. selection means, to selectively place said lenses in and remove said lenses from the optical path to the sensor assembly, for providing a plurality of viewing capabilities for the camera.

6. The camera of claim 2, further including:
   a. magnification changing means,
   b. aperture changing means,
   c. focusing means, and
   d. light dispersion changing means, wherein at least two of said magnification changing means, said aperture changing means, said focusing means, and said light dispersion changing means are set in fixed relationships, to selectably preset a plurality of sets of viewing characteristics of the camera for a plurality of standardized viewing situations.

7. The camera of claim 1, wherein said reflector is one or more member of the set consisting of mirrors and prisms.

8. The camera of claim 1, wherein said reflector is a non-inverting prism.

9. The camera of claim 1, wherein said reflector is a roof prism.

10. The camera of claim 1, further including magnification changing means.

11. The camera of claim 10, wherein said magnification changing means permits selection between preset values of magnification.

12. The camera of claim 1, further including aperture setting means.

13. The camera of claim 12, wherein said aperture setting means permits selection between preset values of aperture.

14. The camera of claim 1, further including focusing means.

15. The camera of claim 14, wherein said focusing means permits selection between preset values of focus.

16. The camera of claim 1, further including a main lens assembly, for suitably tailoring major characteristics of images captured by the camera.

17. The camera of claim 16, further including:
   a. magnification changing means,
   b. aperture changing means,
   c. focusing means, and
   d. light dispersion changing means, wherein at least two of said magnification changing means, said aperture changing means, said focusing means, and said light dispersion changing means are set in fixed relationships, to selectably preset a plurality of sets of viewing characteristics of the camera for a plurality of standardized viewing situations.

18. The camera of claim 1, further including optical filter means.

19. The camera of claim 1, wherein said sensor assembly is a charge coupled device.

20. The camera of claim 1, further including illumination means, for illuminating the area viewed by the camera.

21. The camera of claim 20, wherein said illumination means further includes:
   a. a light source; and
   b. light guide means, having defined therein
      i. a source end, located proximate said light source, and
      ii. a terminal end located generally proximate said view port in the housing, to convey and suitably direct light energy from said light source to exit at said view port.

22. The camera of claim 21, further including light dispersion means, located at either of the set of locations consisting of said source end and said terminal end of said light guide, to suitably tailor a field of illumination of said illumination means to encompass the field of view of the camera.

23. The camera of claim 22, further including light dispersion changing means, to suitably tailor illumination coverage provided by said illumination means over the camera viewing area.

24. The camera of claim 1, further including:
   a. magnification changing means,
   b. aperture changing means,
   c. focusing means, and
   d. light dispersion changing means, wherein at least two of said magnification changing means, said aperture changing means, said focusing means, and said light dispersion changing means are set in fixed relationships, to selectably preset a plurality of sets of viewing characteristics of the camera for a plurality of standardized viewing situations.

25. The camera of claim 1, wherein said utility conveying means further includes universal connection means, to join a conduit subsystem of said dental tool to said utility conveying means of the camera.

26. A modular dental video camera for use in displaying images from inside a patient's mouth onto a monitor, comprising:
   a. an end module, having a view port;
   b. a main housing, having a distal end and a handle portion;
   c. attachment means, for securing said end module to said distal end of the main housing, to permit selectively changing the end module;
   d. a sensor assembly, mounted in said distal end of the main housing and optically aligned substantially along a longitudinal axis through said housing, for converting to data signals image information which has entered the camera through said view port in the end module;
   e. a reflector located in the optical path to said sensor assembly and suitable for directing images from at least 90 degrees away from said longitudinal axis into said sensor assembly; and
   f. utility conveying means, for conveying power and control signals into and data signals out of the camera.

27. The camera of claim 26, further including:
   a. an objective lens assembly, located at said view port of the end module, for suitably tailoring initial characteristics of images captured by the camera; and
   b. a main lens assembly, located in the main housing and in the optical path between said reflector and said sensor assembly, for suitably tailoring major characteristics of images captured by the camera.

28. A modular dental video camera for use in displaying images from inside a patient's mouth onto a monitor comprising:
   a. a frame, having a distal end and a proximal end;
   b. a sensor assembly, mounted in said distal end of the frame and optically aligned substantially along a longitudinal axis through said housing;
   c. a reflector located in the optical path to said sensor assembly and suitable for directing images from at least 90 degrees away from said longitudinal axis into said sensor assembly;
   d. a sleeve, having a distal end, a proximal end, and a handle portion, wherein
      i. said distal end of the sleeve includes a transparent window portion;
   e. attachment means, for connecting said proximal end of the sleeve to said proximal end of the frame when the frame is inserted into the sleeve, such that said window portion of the sleeve distal end is in the optical path to said sensor assembly; and
   f. utility conveying means, for conveying power and control signals into and data signals out of the camera.

29. The camera of claim 28, further including:
   a. an objective lens assembly, located at said distal end of said frame, in the optical path to said sensor assembly, for suitably tailoring initial characteristics of images captured by the camera; and
   b. a main lens assembly, located in the frame, in the optical path between said reflector and said sensor assembly, for suitably tailoring major characteristics of images captured by the camera.

30. A dental video camera for use in displaying images from inside a patient's mouth onto a monitor, comprising:
   a. a housing, having defined therein
      i. a handle portion, and
      ii. a distal end, which includes a view port;
   b. a sensor assembly, mounted in said distal end of the housing and optically aligned substantially along a longitudinal axis through said housing, for converting to data signals images which have entered the camera through said view port;
   c. a permanently integrated dental tool, for performing dental treatment while the camera is used to observe; and
   d. utility conveying means for conveying power and control signals into and data signals out of the camera.

31. A dental video camera for use in displaying images from inside a patient's mouth onto a monitor, comprising:
   a. a housing, including attachment means for in modular manner temporarily joining another dental tool with said camera;
   b. said housing having defined therein
      i. a handle portion, and
      ii. a distal end, which includes a view port;
   c. a sensor assembly, mounted in said distal end of the housing and optically aligned substantially along a longitudinal axis through said housing, for converting to data signals images which have entered the camera through said view port; and
   d. utility conveying means for conveying power and control signals into and data signals out of the camera.

* * * * *